United States Patent [19]

Kagawa et al.

[11] Patent Number: 5,726,045
[45] Date of Patent: Mar. 10, 1998

US005726045A

[54] MATERIALS AND METHODS FOR CONVERTING DNA TO CO-DNA

[76] Inventors: Haruo Kagawa; Kazuko Kagawa, both of 13-29 Minami-Inoue-cho, Higashino, Yamashina-ku Kyoto 607, Japan; Hiroaki Tokimatsu, Haimu-Fushimi C-213, Shimomisu-Yamadono-1, Yoko-Oji, Fushimi-ku Kyoto 612, Japan

[21] Appl. No.: 567,934

[22] Filed: Dec. 6, 1995

[51] Int. Cl.$^6$ ............... C12P 19/34; C12N 9/00; C12N 9/10; C12N 9/04
[52] U.S. Cl. ............ 435/91.1; 424/94.5; 435/183; 435/193; 435/190
[58] Field of Search ............ 424/94.5; 435/91.1, 435/183, 193

[56] References Cited

PUBLICATIONS

Rossmann et al., *Nature*, 250, 194–199 (1974).
Rossmann et al., "The Enzymes," vol. 11, 61–102 (1975).
Birktoft et al., *Proc. Natl. Acad. Sci. U.S.*, 79, 6166–6170 (1982).
Kagawa et al., *Eur. J. Biochem.*, 129, 487–498 (1983).
Kagawa et al., *Eur. J. Biochem.*, 129, 499–507 (1983).
Kagawa et al., "The Converting Activity from DNA to Deoxy–GNA in the Developmental Chick Brain," Annual Reports of the Institute for Virus Research of Kyoto University, Report for 1989, vol. 32, p. 12.
Kagawa et al., "A New Feature of the Structure of the Monomer of the Brain DNA," Annual Reports of the Institute for Virus Research of Kyoto University, Report for 1990, vol. 33, pp. 45–46.
Kagawa et al., "Conversion of DNA to Carbonyl–Additional–DNA (CO–DNA) in the Maturated Cerebrum and Mitotically Inactive Permanent Cells," Annual Reports of the Institute for Virus Research of Kyoto University, Report for 1991, Vo. 34, pp. 67–68.
Kagawa et al., "Studies of a Novel Deoxynucleic Acid, CO–DNA," Annual Reports of the Institute for Virus Research of Kyoto University, Report for 1992, vol. 35, pp. 46–47.
Kagawa et al., "Conversion Reaction of DNA to CO–DNA," Annual Reports of the Institute for Virus Research of Kyoto University, Report for 1993, vol. 36, pp. 51–52.

Kagawa et al., "Purification of the enzyme that convert DNA to CO–DNA," Annual Reports of the Institute for Virus Research of Kyoto University, Report for 1994, vol. 37, p. 61.

Kagawa et al., "Possibility of the converstion of the DNA from *E. coli* into 'deoxyglucose nucleic acid'" (Abstract No. 4G–22), Abstracts for the annual meeting of the Japanese Molecular Biology Organization, 12th Annual Meeting, Nov. 29–Dec. 2, 1989 (English translation).

Kagawa et al., "Structure of 'deoxyglucose nucleic acid' in brain," (Abstract No. 4158), Abstracts for the annual meeting of the Japanese Molecular Biology Organization, 13th Annual Meeting, Nov. 26–29, 1990 (English translation).

Kagawa et al., "The constituting sugar of the cerebral 'DNA' is identical to synthesized metasaccharinic acid (3–deoxy––hexonic acid)," (Abstract No. 1140), Abstracts for the annual meeting of the Japanese Molecular Biology Organizatioin, 14th Annual Meeting, Dec. 17–20, 1991 (English translation).

Kagawa et al., "DNA is converted to CO–DNA in the 'Permanent Cells,'" (Abstract No. 1192), Abstracts for the annual meeting of the Japanese Molecular Biology Organization, 15th Annual Meeting, Dec. 7–10, 1992 (English translation).

Kagawa et al., "Mechanism of conversion of DNA to CO–DNA," (Abstract No. 3217), Abstracts for the annual meeting of the Japanese Molecular Biology Organization, 16th Annual Meeting Dec. 16–19, 1993 (English translation).

Kagawa et al., "Purification of the enzymes that convert DNA to CO–DNA," (Abstract No. 2–20–466), Abstracts for the annual meeting of the Japanese Molecular Biology Organization, 17th Annual Meeting, Dec. 13–16, 1994 (English translation).

*Primary Examiner*—Robert A. Wax
*Assistant Examiner*—Einar Stole
*Attorney, Agent, or Firm*—Marshall, O'Toole, Gerstein, Murray & Borun

[57] ABSTRACT

Materials and methods for conversion of traditional DNA to CO-DNA are presented. Such materials and methods are useful to inhibit cell division and to monitor conversion of DNA to CO-DNA.

4 Claims, 9 Drawing Sheets

FIG. 1A
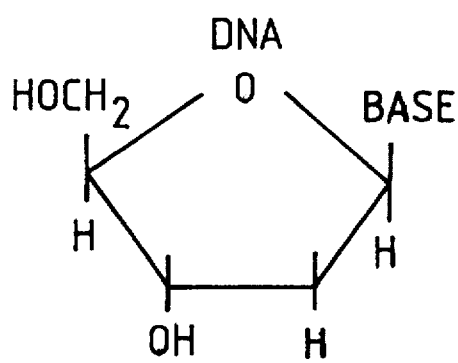
FIG. 1B
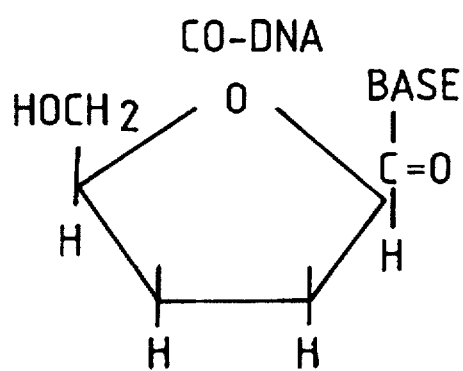
FIG. 2
| MATERIALS | DEOXYRIBOSE % DETECTED BY GAS CHROMATOGRAM |
|---|---|
| AUTHENTIC D-AMP | 100 |
| CEREBELLUM | 80-88 |
| MEDULLA OBLONGATA | 78 |
| LIMB MUSCLE | 85 |
| LIVER | 100 |
| PERMANENT CELLS | |
| CEREBRUM | 20-30 |
| HEART MUSCLE | 10-22 |
| LENS | 22 |

$C^{14}$ LABELED SUGAR CONSTITUENT FROM DEOXYNUCLEOTIDE Ap

ENZYMES SEPARATION IN DEAE SEPHADEX

SEPARATION IN Q SEPHAROSE

Q SEPHAROSE 0.01M FRACTION 5,726,045

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Ala Lys Val Ala Val Leu Gly Ala Ser Gly Gly Ile Gly Gln Pro Leu
 1               5                  10                  15
Ser Leu Leu Leu Lys Asn Thr Pro Leu Thr Gly Gln
            20                  25
```

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Glu Asn Tyr Pro Leu Asp
 1               5
```

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Glu Lys Phe Leu Lys Gly Asn Ile Gln Asp
 1               5                  10
```

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Glu Val Ile Asp Gly Ala Asn Val His
 1               5
```

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Glu  Ala  Asn  Gly  Asp  Asp  Phe
1                 5
```

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Glu  Gln  Val  Ile  Thr  Gln  Asn
1                 5
```

( 2 ) INFORMATION FOR SEQ ID NO:7:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Glu  Ala  Gly  Asp  Gly  Xaa  Asp
1                 5
```

( 2 ) INFORMATION FOR SEQ ID NO:8:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Glu  Ala  Met  Asn  Asn  Pro  Phe  Asp
1                 5
```

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Lys  Gln  Leu  Gly  Asp  Asn
1                 5
```

(2) INFORMATION FOR SEQ ID NO:10:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:10:

Glu Ala Asn Gly Asp Asp Phe
1               5

(2) INFORMATION FOR SEQ ID NO:11:

(i) SEQUENCE CHARACTERISTICS:
(A) LENGTH: 13 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:11:

Ile Val Val Ile Phe Ser Pro Asn Glu Glu Gln Asn Met
1               5                       10

MATERIALS AND METHODS FOR CONVERTING DNA TO CO-DNA

FIELD OF THE INVENTION

The present invention relates to materials and methods for converting DNA to CO-DNA.

BACKGROUND OF THE INVENTION

Cells may be placed into one of two primary categories. Permanent cells are those that are generated in appropriate numbers during embryogenesis and are retained throughout life. They do not divide and are not replaced if they are lost. Neural cells in the cerebrum and cardiac muscle cells are specific types of permanent cells. Proliferating cells are those that continue to divide throughout life. They are consistently reproduced and are replaced if they are lost. Cancer cells are a specific type of proliferating cell. In most cases, cancer cells divide at a rate that is many times as fast as that of corresponding non-cancerous proliferating cells.

In cells that retain the ability to divide, DNA assumes the traditional 2-deoxyribose configuration, wherein the nitrogenous base is attached at the 1' carbon of the 2-deoxyribose sugar (FIG. 1A). For purposes of the present invention, traditional 2-deoxyribose DNA is referred to simply as DNA. The structure and replication of DNA is well known.

Several proto-oncogenes are known that encode various cellular growth factors (or growth factor subunits) that are thought to stimulate cell proliferation. When those genes are overexpressed, uncontrolled cell proliferation may result, leading to tumor formation. However, the cellular mechanisms that control cell division in healthy cells versus cancer cells are poorly understood.

There is, therefore, a need in the art for a method for halting cell division in certain proliferating cells, such as cancer cells. The present invention provides methods and materials for converting DNA to CO-DNA which are useful for stopping cell division in proliferating cells.

SUMMARY OF THE INVENTION

The present invention provides enzymes for converting DNA to CO-DNA. Conversion of DNA to CO-DNA reduces or eliminates the cell's ability to divide. CO-DNA is a form of DNA in which a carbonyl group is attached to the 1' carbon of the sugar constituent of DNA and to the nitrogenous base. A CO-DNA nucleoside is shown in FIG. 1B.

In a preferred embodiment, an enzyme according to the invention has a molecular weight of about 43,000 Daltons and has an N-terminal sequence comprising the residues AKVAVLGASGGIGQPLSLLLKNTPLTGQ (SEQ ID NO: 1). Upon V8 proteinase digestion, an enzyme according to the present invention produces one or more fragments, including one or more fragments selected from the group consisting of ENYPLD (SEQ ID NO: 2), EKFLKGNIQD (SEQ ID NO: 3), EVIDGANVH (SEQ ID NO: 4), EANGDDF (SEQ ID NO: 5), EQVITQN (SEQ ID NO: 6), EAGDGXD (SEQ ID NO: 7), and EAMNNPFD (SEQ ID NO: 8) Upon lysilendopeptidase digestion a fragment having the sequence KQLGDN (SEQ ID NO: 9) is produced.

The invention also provides methods for converting DNA to CO-DNA, comprising exposing DNA to enzymes capable of catalyzing the conversion of DNA to CO-DNA in the presence of glucose or 3-deoxyhexonic acid and an appropriate buffer or cell culture system. The invention also provides a method for treating cancer, comprising the administration of enzymes capable of converting DNA to CO-DNA to a patient suspected of having cancer. The enzyme preparation may include a pharmaceutically-acceptable carder and may be administered by injection, orally, by absorption, or by targeted drug delivery.

Methods according to the invention may also be used to inhibit cell proliferation by exposing cells to enzymes capable of convening DNA to CO-DNA.

Based upon methods and materials disclosed herein, it is possible to construct probes (based upon the N-terminal sequence of the enzyme characterized below) to probe cDNA libraries for the gene or genes encoding the converting enzyme or enzymes.

Additional embodiments and advantages of the invention will be apparent to the skilled artisan upon consideration of the detailed description thereof.

DESCRIPTION OF THE DRAWINGS

FIG. 1A shows a traditional DNA nucleoside.

FIG. 1B shows a CO-DNA nucleoside.

FIG. 2 is a table showing the percentage of 2-deoxyribose in cells obtained from various tissue samples.

DETAILED DESCRIPTION OF THE INVENTION

When deoxynucleic acids were isolated from various tissues and the sugar constituents were analyzed, permanent cells contained very small amount of 2-deoxyribose as shown in FIG. 2. Analysis of constituent sugars and NMR data revealed that permanent cells contain a separate type of DNA that was termed CO-DNA. That name is based upon the characteristic structure of CO-DNA, wherein a carbonyl group is inserted between the 1' carbon of the sugar and the nitrogenous base. CO-DNA differs from 2-deoxyribose DNA in that the constituent sugar in CO-DNA is a deoxyhexose and not a 2-deoxyribose. The 1' carbon of the sugar is directly attached to a carbonyl group, the carbon of which forms the attachment to the nitrogenous base portion of the nucleotide. The structures of DNA and CO-DNA are compared in FIGS. 1A and 1B. In permanent cells, DNA is predominantly in the form of CO-DNA. Based upon its strong presence in permanent cells and its relative obscurity in proliferating cells, it was proposed that the presence of CO-DNA was responsible for the non-proliferation of permanent cells in, for example, the cerebrum and heart muscle. FIG. 2 shows the relative distribution of traditional DNA in various tissues. As shown in FIG. 2, the percentage of DNA in permanent cells (cerebrum, heart muscle, lens) is considerably less than that in proliferating cells.

The present invention provides materials and methods for conversion of DNA to CO-DNA. Conversion of DNA to CO-DNA is useful as a mechanism for reducing or eliminating the ability of the cell to divide. Using methods of the invention, one may convert a highly-proliferative cancer cell to a cell that is unable to divide, thus eliminating or greatly reducing the harmful effects of the cancer. The following examples are illustrative of methods according to the invention.

EXAMPLE 1

Isolation and Structural Characterization of CO-DNA

Nucleotides were isolated from chick and bovine cerebral DNA. Cerebral nucleic acids were incubated in 20 ml of a solution comprising 50 µl of nuclease P1 (400 U/ml, Seikagaku Kogyo Co., Japan), 25 µl of 0.5M sodium acetate buffer (pH 4.5), and 25 µl of 0.1M $ZnSO_4$ at 55°C. for 2 hours. After shaking with chloroform, the solution was concentrated in a rotary evaporator and applied to an HPLC column (Cosmosil 5C18, 1×25 cm, Nakarai Chemicals, Japan). Elution was carried out with 5% methanol and 5 mM $KH_2PO_4$ at 35° C. Cer-deoxynucleotides were alesalted by passing them through a Bio-Gel P-2 column (1×100 cm, 200–400 mesh, Bio-Rad) with distilled water and then incubated in a 0.3 ml solution comprising 30 µl sweet potato acid phosphatase (Type X, Sigma, 10 mg/ml) and 10 µl of 1M sodium acetate buffer (pH 4.5) for 2 hours at 37° C. After incubation, the sample was applied to the same Cosmosil column described above and eluted with 10% methanol.

Figure 3:
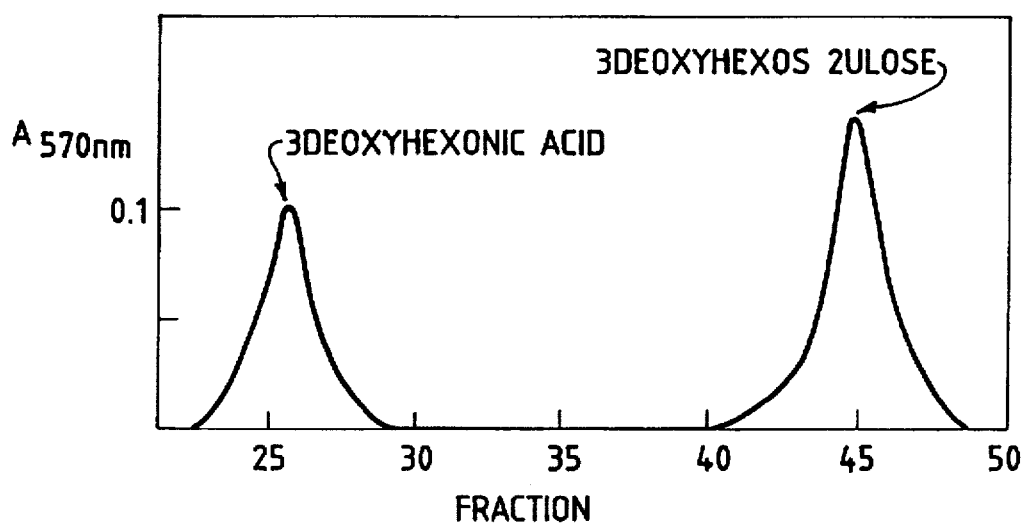
FIG. 3 is a graph showing the separation of CO-DNA sugars by Shodex 801 column chromatography.

The constituent sugars were then isolated by acid hydrolysis after dephosphorylation with acid phosphatase. Two different sugars were obtained that were clearly separated by Shodex 801 column chromatography as shown in FIG. 3. Further analysis identified the sugars as 3-deoxyhexonic acid and 3-deoxyhexos-2-ulose. When deoxynucleosides were boiled in 0.1M HCl for 1 minute, 3-deoxyhexonic acid was produced. However, when deoxynucleosides were boiled in 0.4M formic acid for 5 minutes, 3-deoxyhexos-2-ulose was predominant.

On the basis of these data and NMR data, the structure of CO-DNA was elucidated. The data revealed that CO-DNA retains a double-helical polymeric structure, a nucleoside of which is shown in FIG. 1B.

EXAMPLE 2

A Method to Detect the Conversion from DNA to CO-DNA

According to the present invention, methods are presented for the detection of the conversion from DNA to CO-DNA. Hoechst 33342 dye is used in the art to quantify DNA due to the ability of the dye to bind double stranded DNA. E5 DNA was prepared from 5-day chick embryo brains and was treated with RNase to remove RNA. DNA (E5) was isolated from chick embryo brains by homogenizing 30 brains obtained from 5-day embryos in 50 ml of buffer containing 30 mM Tris-HCl (pH 7.5) and 2 mM EDTA using an Ultra-Turrax homogenizer. After homogenization, 0.25% SDS and 200 µg/ml proteinase K were added to the suspension which was then incubated at 37° C. for 3 hours. Nucleic acids were extracted with an equal volume of 80% phenol and the aqueous phase was pooled after centrifugation. Two volumes of ethanol and 0.1 volume of 0.5M sodium acetate buffer (pH 4.5) were added to the extract and the DNA was precipitated. Preparations of CO-DNA were derived from either 1-day old chick cerebrum or adult bovine cerebrum in a similar manner.

Figure 4:
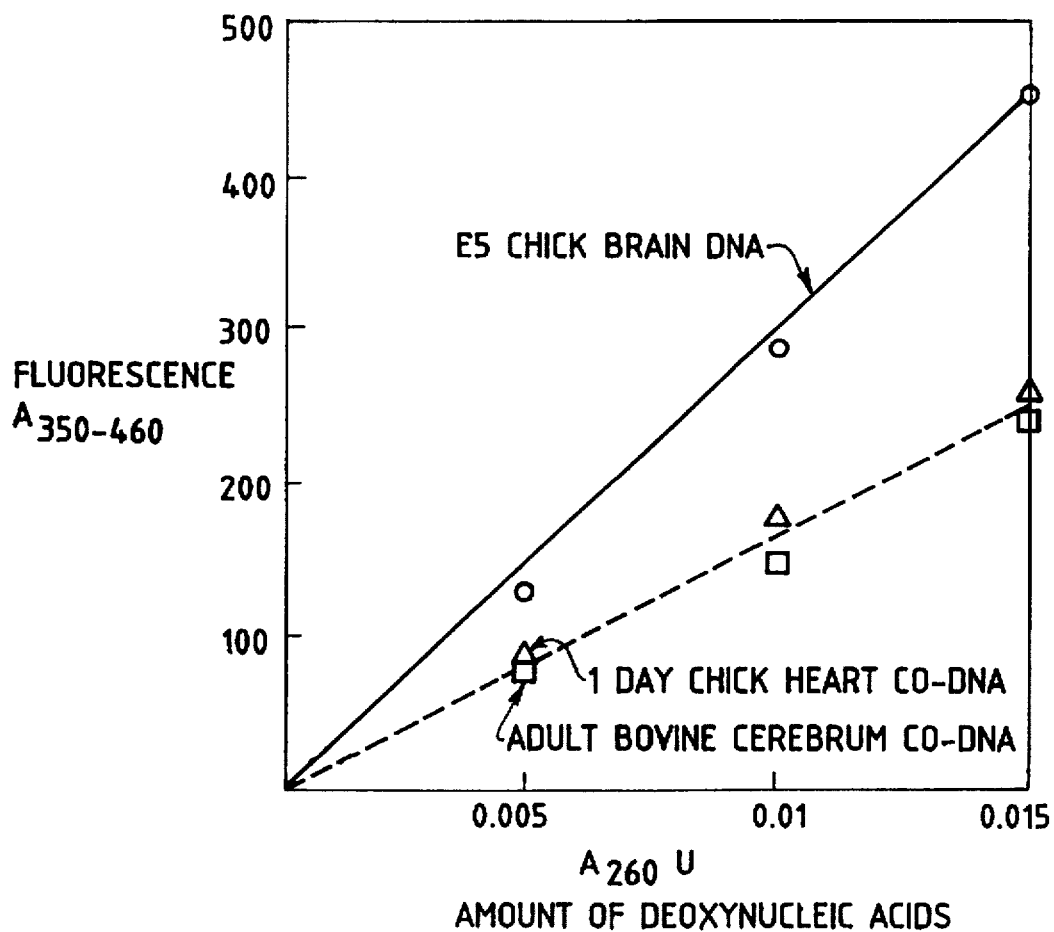
FIG. 4 is a graph showing fluorescence of Hoechst dye produced by DNA and CO-DNA.

A stock solution of Hoechst 33342 dye was made at a concentration of 0.1 mg/ml in 25 % ethanol and was stored at 4° C. The stock solution was diluted prior to use by mixing 10/µl stock solution with 0.1 ml of 0.5M sodium phosphate buffer (pH 6.5) and 10 ml 25% ethanol. The method was carried out as described below. In general, a buffered composition comprising DNA, glucose or 3-deoxyhexonic acid, $MgCl_2$, $CaCl_2$, NaCl, and an extract containing enzyme was combined with diluted stock solution containing the Hoechst dye. Fluorescent intensity was measured using a fluorimeter (Spectro-fluorometric-detector Model RF-550, Shimadzu Corporation, Japan) at 460 nm using an excitation source set at 350 nm. As shown in FIG. 4, the intensity of fluorescence when CO-DNA was exposed to Hoechst dye was approximately 60% of the fluorescence obtained with DNA. The reduction in fluorescent intensity observed when the method is applied to CO-DNA is a convenient method for quantifying the conversion of DNA to CO-DNA and an example of the use of the method is shown below.

Figure 5:
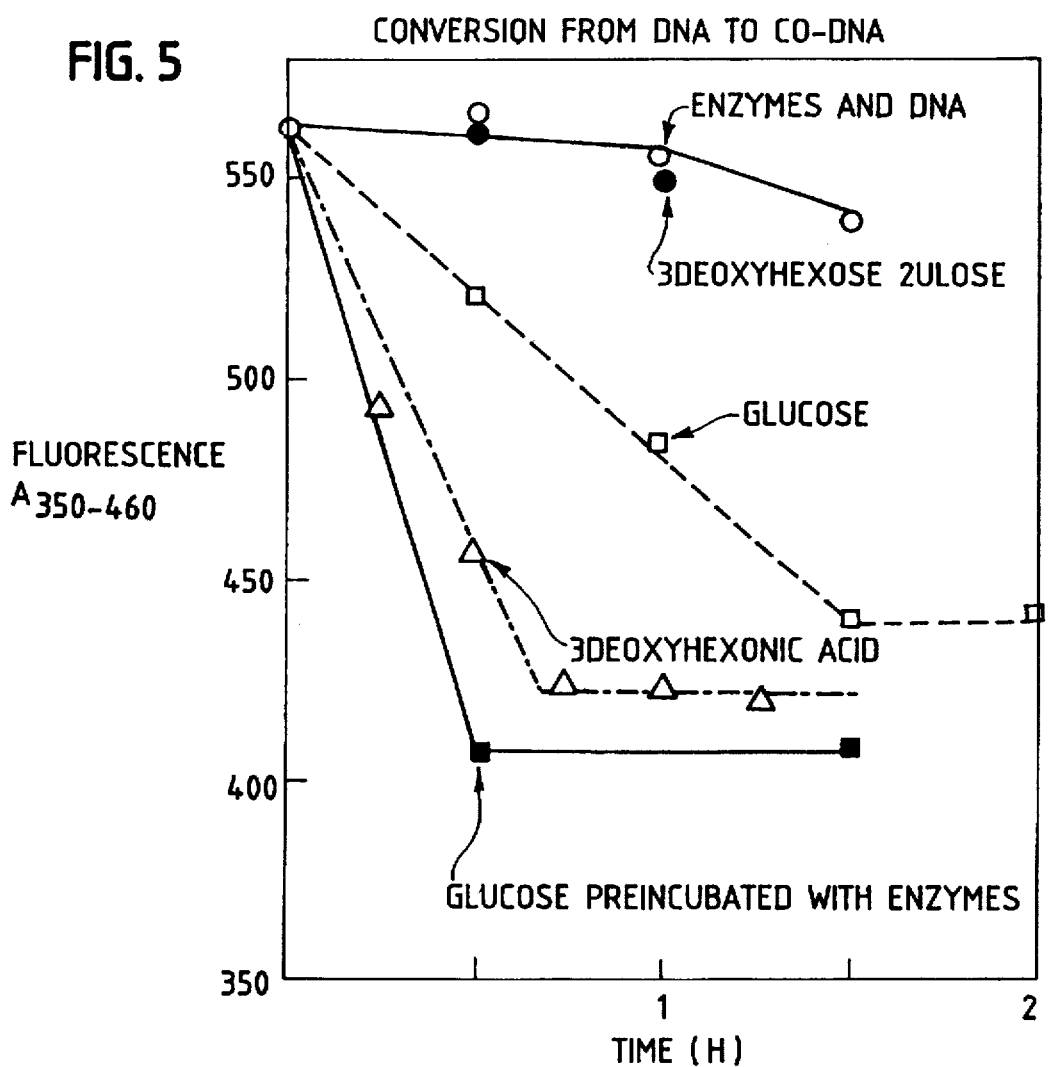
FIG. 5 is a graph showing conversion to CO-DNA in the presence of various starting materials.

Experiments determined that $Ca^{2+}$ is required for converting-enzyme activity. Thus, a reaction mixture was prepared in 30 µl volumes, each comprising 10 mM Tris/HCl, pH 7.5, 1 mM $MgCl_2$, 1 mM $CaCl_2$, 0.1M NaCl, E5 chick brain DNA and a 10 µl aliquot of the crude enzyme preparation described below suspended in buffer comprising 10 mM Tris-HCl (pH 7.5), 1 mM $MgCl_2$, 0.2 mM $CaCl_2$, 0.05M NaCl, and 0.1M ammonium sulfate. The reaction mixture was allowed to incubate with either glucose without enzymes (open squares in FIG. 5), 3-deoxyhexonic acid without enzymes (open triangles in FIG. 5), glucose and enzymes (closed squares in FIG. 5), 3-deoxyhexose-2-ulose (closed circles in FIG. 5), or enzymes and DNA (open circles in FIG. 5) for 0–2 hours as shown in FIG. 5. Then, 50 µl of 0.05M sodium phosphate buffer (pH 6.5) and 0.5 ml of the diluted stock dye solution (described above) were added to the reaction mixture. The resulting mixture was maintained at room temperature in the dark for 15 minutes and then the fluorescence intensity was measured as described above.

Experiments, the results of which are shown in FIG. 5, revealed that when DNA was incubated in the presence of enzymes alone, no conversion occurred (open circles in FIG. 5). When either glucose or 3-deoxyhexonic acid was added to the incubation mixture, the conversion of DNA to CO-DNA was detected (open squares and open triangles, respectively in FIG. 5). On the contrary, however, no conversion occurred when 3-deoxyhexos-2-ulose was added as shown by the closed circles in FIG. 5. 3-deoxyhexos-2-ulose was, however, obtained by acid hydrolysis of CO-DNA.

EXAMPLE 3

The Steps Involved in the Conversion of DNA to CO-DNA

Figure 6:
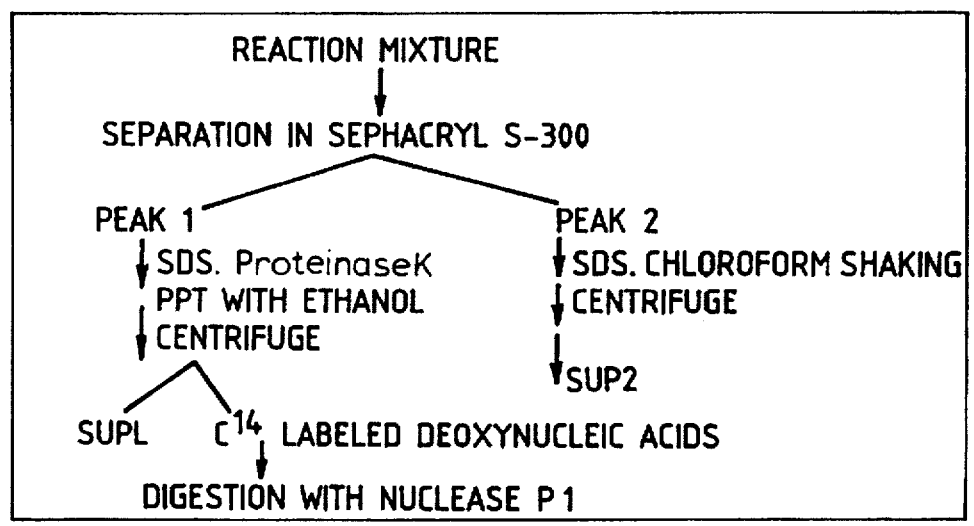
FIG. 6 is a flow chart of the procedures of analysis of intermediates in the conversion of DNA to CO-DNA.
Figure 7A:
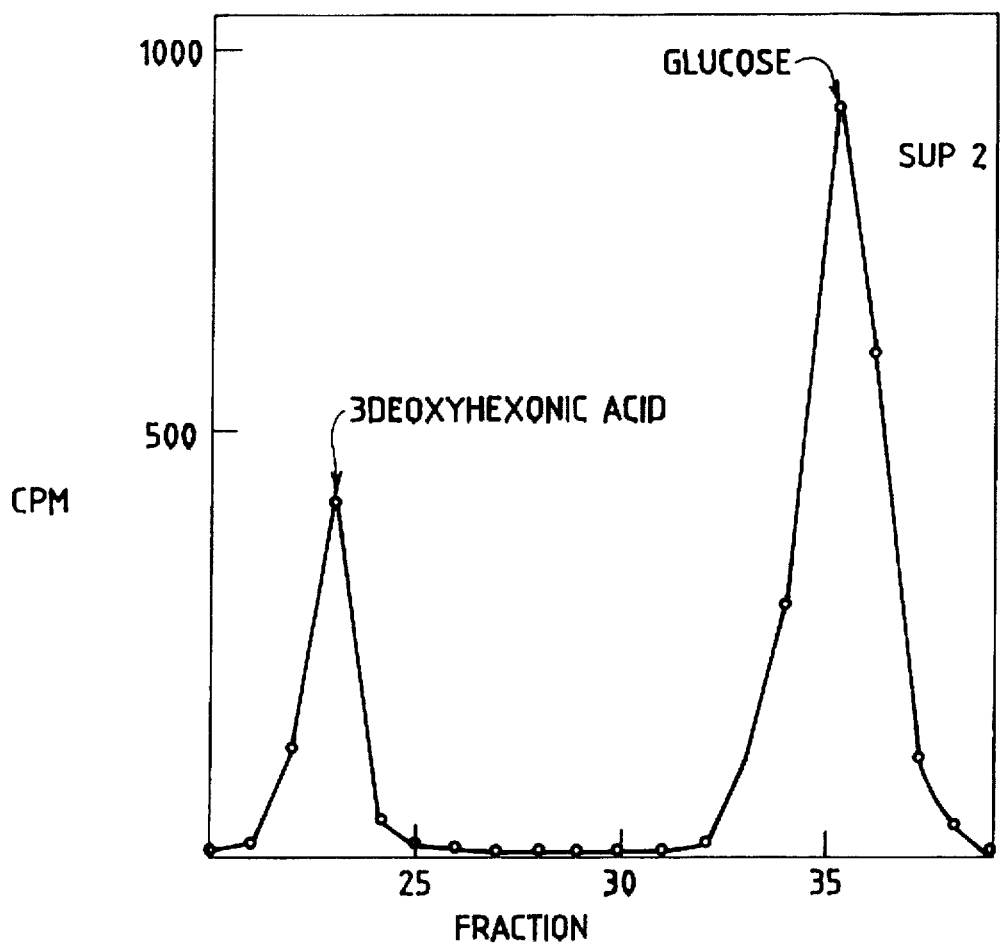
FIGS. 7A and 7B show detection of $^{14}C$ in intermediates in the conversion of DNA to CO-DNA.
Figure 7B:
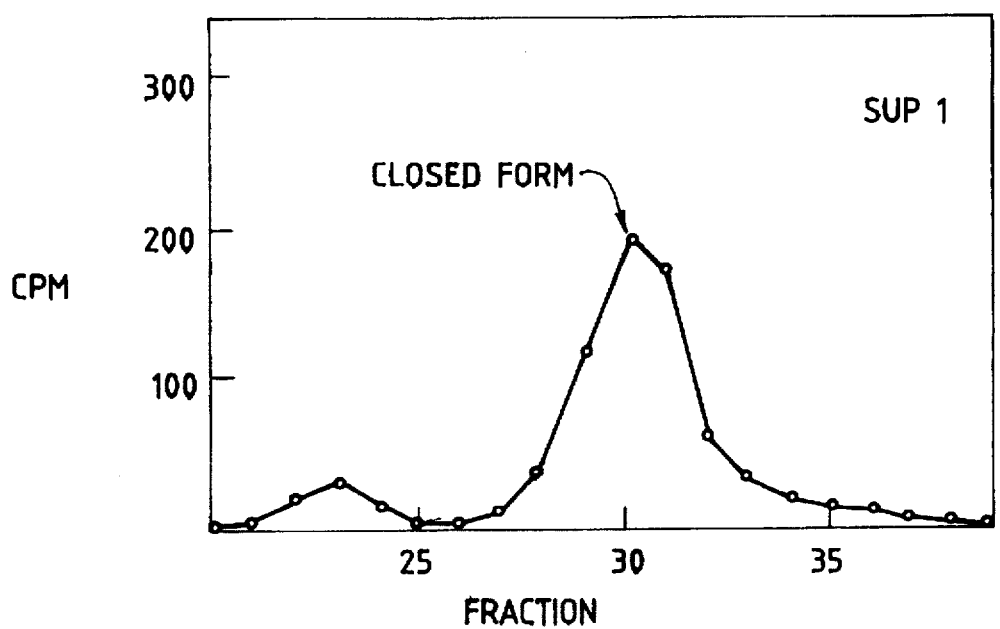
Figure 8:
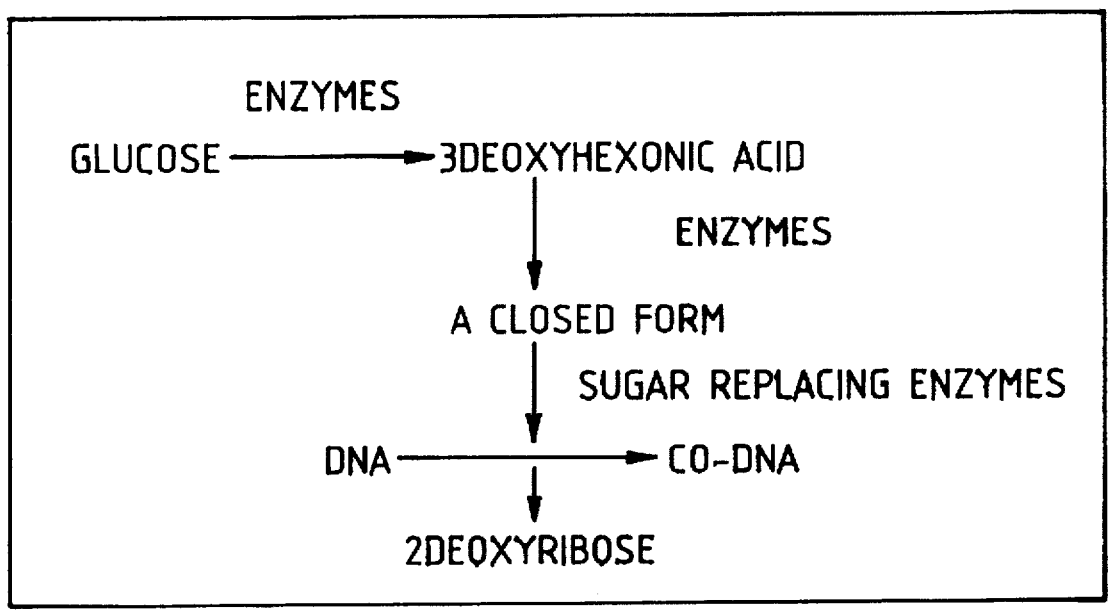
FIG. 8 is a flow chart showing the steps in the conversion of DNA to CO-DNA.

Uniformly labeled $^{14}C$ glucose was incubated with partially purified enzymes in the presence of DNA. After incubating at 37° C. for several hours, the reaction mixture was separated on Sephacryl S-300 and two peaks were resolved. Material from the first peak was digested with proteinase k and precipitated with ethanol. The precipitate was centrifuged and $^{14}$C-labeled deoxynucleic acids were isolated in the pellet. A second peak was shaken in chloroform and centrifuged to produce a second supernatant. A schematic diagram showing the isolation procedure is provided in FIG. 6. $^{14}$C-labeled 3-deoxyhexonic acid was detected in the reaction mixture (FIG. 7A), showing that labeled glucose in the original reaction mixture was transformed to 3-deoxyhexonic acid. These results are consistent with the presence of 3-deoxyhexonic acid in CO-DNA. Additional evidence indicated that the 3-deoxyhexonic acid is used to produce CO-DNA through an intermediate, the lactone (closed form) of 3-deoxyhexonic acid (FIG. 7B). The reaction thought to be involved in the DNA to CO-DNA conversion are shown schematically in FIG. 8.

EXAMPLE 4

Confirmation of the Conversion from DNA to CO-DNA

Figure 9:
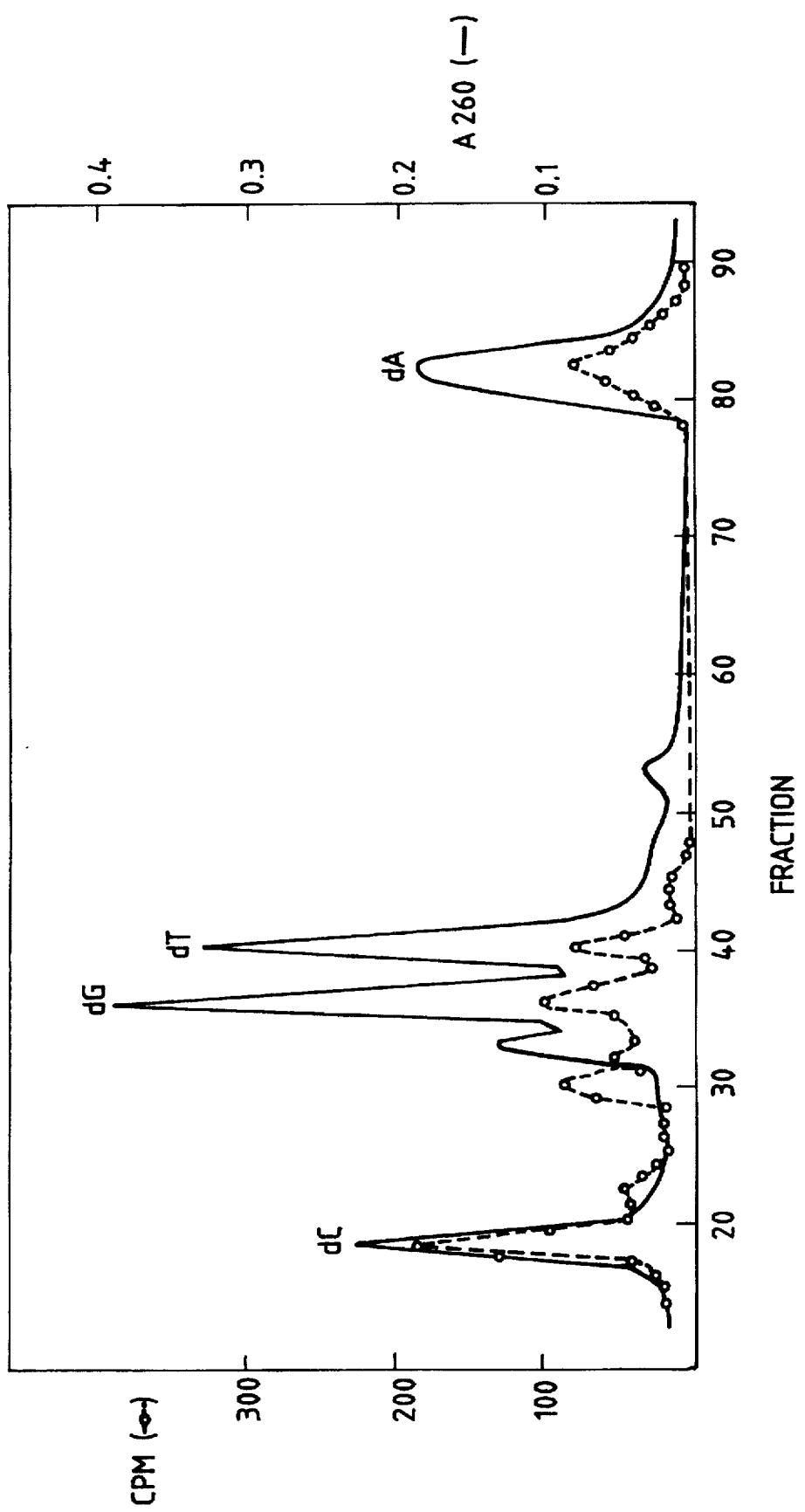
FIG. 9 is a graph showing that all four deoxynucleosides were labeled when uniformly labeled $^{14}C$ glucose was used as the substrate for the conversion from DNA to CO-DNA.
Figure 10:
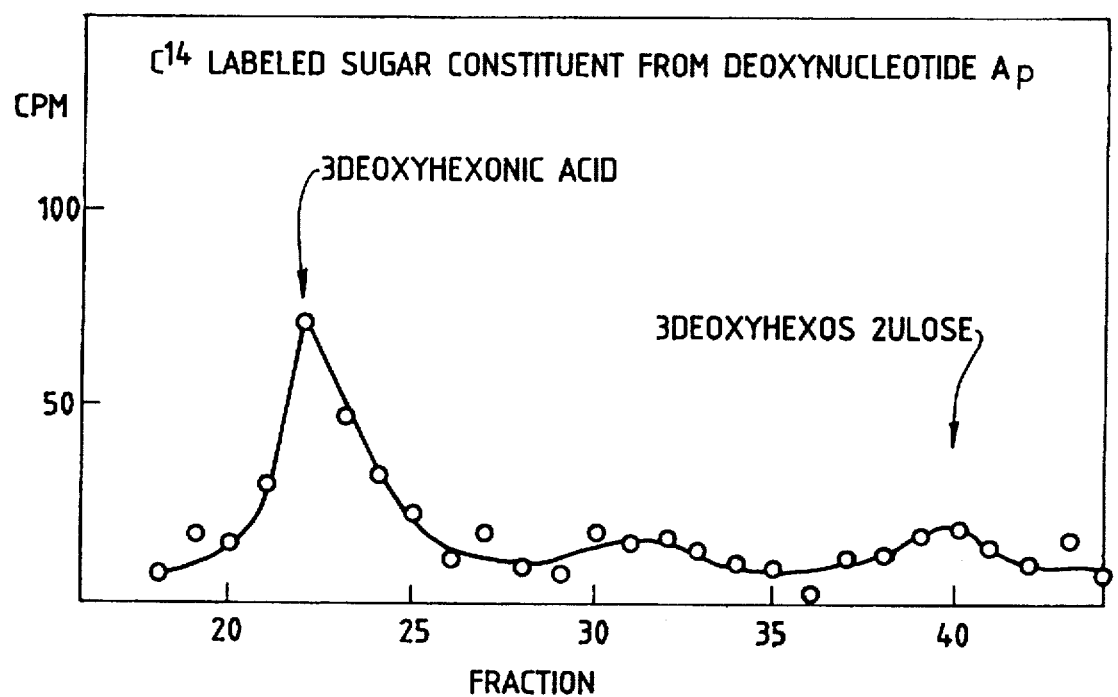
FIG. 10 is a graph showing that 3-deoxyhexonic acid is the major sugar component of CO-DNA.

When $^{14}$C labeled glucose was used as the substrate, labeled carbon was incorporated into CO-DNA. All the nucleotides (or nucleosides) obtained from the labeled CO-DNA were also labeled (FIG. 9) and almost all of the sugar constituent liberated from labeled nucleotides were in the form of 3-deoxyhexonic acid (FIG. 10). These results confirm that CO-DNA was produced in a conversion reaction using carbon from glucose as a substrate.

EXAMPLE 5

Isolation of the Convening Enzyme

Figure 11:
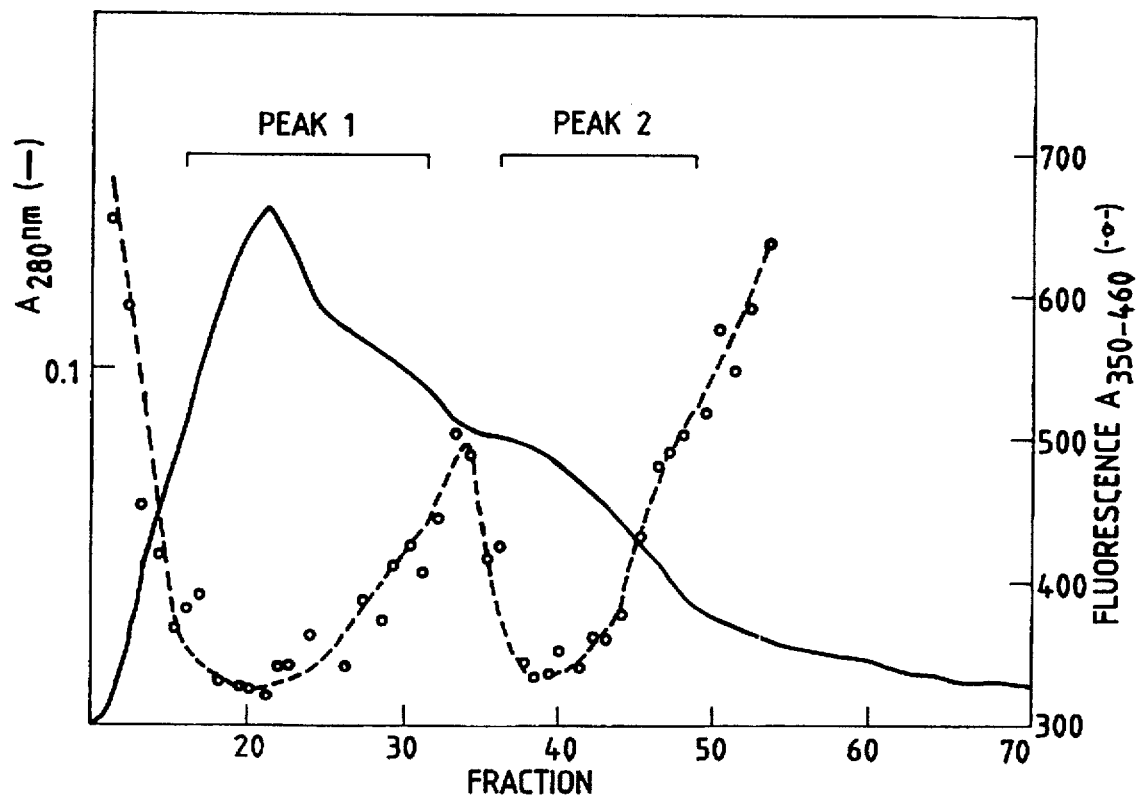
FIG. 11 shows the elution pattern of enzymes separated by DEAE-Sephadex.

Crude enzyme preparations were obtained from either 17 day chick embryo cerebrum or 1 day chick cerebrum. In either case, the cerebrums of 20 chicks were suspended in a 100 ml homogenization buffer comprising 10 mM Tris/HCl (pH 7.5), 2.5 mM MgCl$_2$, 0.1 mM CaCl$_2$, 0.1% Nonidet P-40, and 0.25M sucrose. Homogenization speed and time were controlled such that cells were disrupted but nuclei remained intact as viewed under a phase-contrast microscope. Nuclei were collected by centrifugation at 500×g for 10 minutes. Pelleted nuclei were suspended in 50 ml of a buffer comprising 10 mM Tris/HCl (pH 7.5), 1 mM MgCl$_2$, 0.2 mM CaCl$_2$, and 0.5M ammonium sulfate and stirred for 24 hours at 4° C. The mixture was then centrifuged at 100,000×g for 1 hour in order to remove DNA. The supernatant was collected and concentrated on a rotary evaporator and dialyzed against a buffer containing 10 mM Tris/HCl (pH 7.5), 1 mM MgCl$_2$, 0.2 mM CaCl$_2$, 0.05M NaCl, and 0.1M ammonium sulfate. The resulting material was used as a crude enzyme isolate. In order to further purify the enzyme, the crude isolate was bound to a DEAE-Sephadex column that had been equilibrated with buffer containing 10 mM Tris/HCl (pH 7.5), 1 mM MgCl$_2$, 0.2 mM CaCl$_2$, 0.05M NaCl, and 0.1M ammonium sulfate. Enzyme was eluted using the same buffer. The eluted fractions are shown in FIG. 11. Conversion activity from DNA to CO-DNA is present in peak 1 and peak 2 where the fluorescent intensity was lower. Peak 1 and peak 2 in FIG. 11 were collected and separately dialyzed against buffer comprising 10 mM Tris/HCl (pH 7.5), 1 mM MgCl$_2$, 0.2 mM CaCl$_2$, and 0.01M NaCl.

The two fractions obtained above were used separately to catalyze conversion of DNA to CO-DNA. The fraction obtained from peak 1 was able to catalyze conversion of DNA to CO-DNA using either glucose or 3-deoxyhexonic acid. The material obtained from peak 2 was able to catalyze the conversion only in the presence of 3-deoxyhexonic acid. These results indicated that the conversion enzyme functions as an enzyme complex. One component of the enzyme complex converts glucose to 3-deoxyhexonic acid and the other component catalyzes the conversion of DNA to CO-DNA using 3-deoxyhexonic acid.

Figure 12:
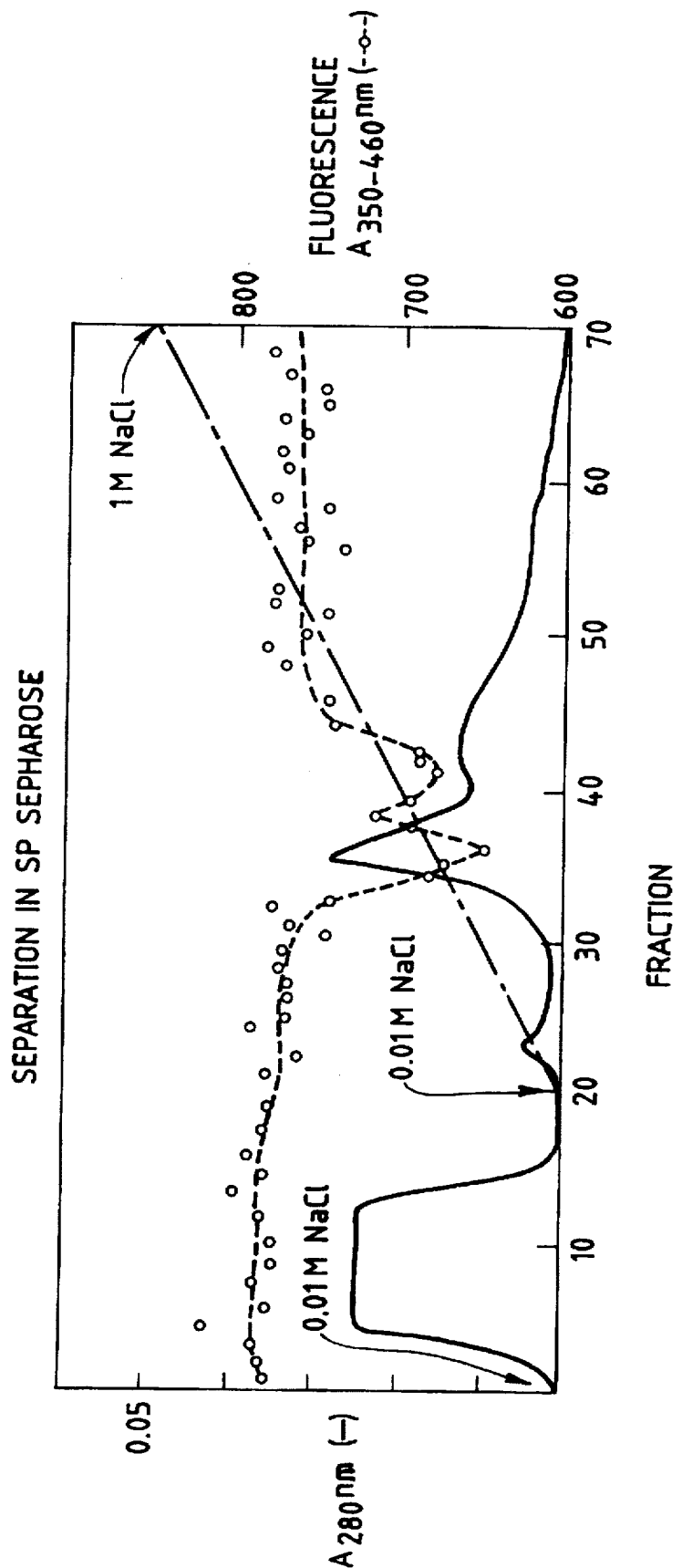
FIG. 12 is a graph showing results of the separation of DNA-to-CO-DNA converting enzymes using SP-Sepharose.
Figure 13:
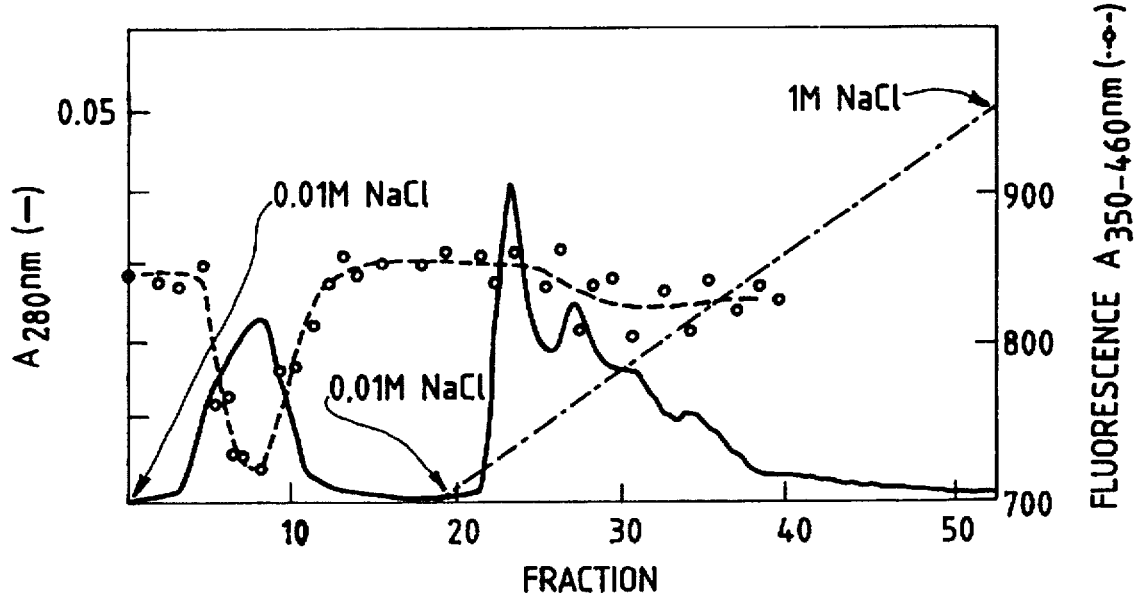
FIG. 13 is a graph showing results of the separation of DNA-to-CO-DNA converting enzymes using Q-Sepharose.

The DEAE-Sephadex fractions (described above) were then separately placed on an SP-Sepharose column and eluted with a linear gradient of NaCl. The fractions obtained are shown in FIG. 12. Fractions obtained from the SP-Sepharose column were collected and dialyzed against buffer comprising 10 mM Tris/HCl (pH 7.5), 1 mM MgCl2, 0.2 mM CaCl2, and 0.01M NaCl. The resulting isolates were bound on a Q-Sepharose column equilibrated with the above-described buffer and eluted with increasing concentrations of NaCl. The resulting fractions are shown in FIG. 13. Activity tests revealed that the conversion enzyme was not absorbed on the column.

Figure 14:
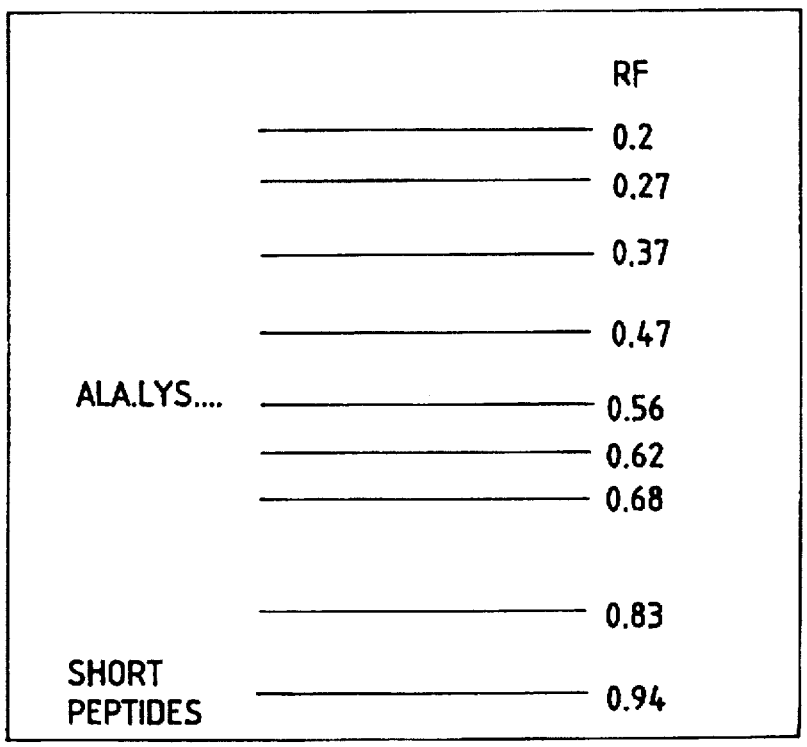
FIG. 14 is a schematic diagram showing results of SDS gel electrophoresis of proteins obtained from the 0.1M fraction of a Q-Sepharose column.

The Q-Sepharose flow-through fraction was collected, concentrated and dialyzed in distilled water. Peptides were separated on a 10% SDS gel, blotted to an Immobilon-P membrane, and stained with Ponceau S according to the method described in Matsudaira, *J. Biol. Chem.*, 262: 10035–10038 (1987), incorporated by reference herein. The results are shown in FIG. 14, wherein a strong band (Rf at 0.56) and less-prominent bands exist at 0.62 and 0.68.

Amino-terminal sequencing of the Rf=0.56 band, having a molecular weight of about 43,000 D, revealed an N-terminal sequence of AKVAVLGASGGIGQ-PLSLLLKNTPLTGQ (SEQ ID NO: 1). A search of the GENBANK database revealed that the portion of SEQ ID NO: 1 from the N-terminus through amino acid number 20 was identical to the N-terminal portion of the C chain of Porcine mitochondrial malate dehydrogenase. The SWISS-PROT database revealed an identity between SEQ ID NO: 1 and amino acids 25–44 of rat mitochondrial malate dehydrogenase. For N-terminal sequencing, the relevant protein band from the SDS gel was transferred to a PVDF membrane and the sequence analyzed using a PSQ-1 system gas-phase sequenator (Shimadzu Co., Kyoto, Japan).

In order to obtain additional information about the Rf 0.56 fraction, it was digested with either V8 protease or lysilendopeptidase and the resulting peptide fragments in each case were purified by reverse-phase HPLC. Some of the smaller fragments produced by V8 protease digestion were sequenced and compared to known protein sequences in the SWISS-PROT database. The sequences obtained were ENY-PLD (SEQ ID NO: 2), EKFLKGNIQD (SEQ ID NO: 3), EVIDGANVH (SEQ ID NO: 4), EANGDDF (SEQ ID NO: 5), EQVITQN (SEQ ID NO: 6), EAGDGXD (SEQ ID NO: 7), and EAMNNPFD (SEQ ID NO: 8). None of these sequences showed any homology to malate dehydrogenase. Lysilendopeptidase digestion produced, among others, the fragment KQLGDN (SEQ ID NO: 9) which also had no homology to malate dehydrogenase. Interestingly, the portion of malate dehydrogenase that is identical to the first twenty amino acids AKVAVLGASGGIGQPLSLLLKNT-PLTGQ of SEQ ID NO: 1 comprises an adenine binding site of NAD in malate dehydrogenase. That region contains two conserved amino acids, corresponding to Leu-6 and Gly-10 in SEQ ID NO: 1.

It is anticipated that from the extract containing the partially-sequenced enzyme, it will be routine practice to obtain an oligonucleotide probe in order to isolate the gene or genes encoding the converting enzyme complex by standard methods in the art. For example, a gene for at least part of the enzyme or enzyme complex may be obtained by PCR using primers corresponding to the peptide sequences EANGDDF (SEQ ID NO: 10) and IVVIFSPNEEQNH (SEQ ID NO: 11).

---

We claim:

1. A method for converting DNA to CO-DNA comprising the step of:
exposing canonical DNA to an isolated and substantially pure enzyme which catalyzes the conversion of DNA to CO-DNA in the presence of an appropriate buffer and a sugar selected from the group consisting of glucose and 3-deoxy hexonic acid.

2. An isolated and substantially pure enzyme capable of catalyzing the conversion of DNA to CO-DNA.

3. The isolated and substantially pure enzyme according to claim 2, wherein the enzyme has a molecular weight of about 43,000 daltons and the N-terminal sequence of the enzyme is AKVAVLGASGGIGQPLSLLLKNTPLTGQ.

4. The isolated and substantially pure enzyme according to claim 3, wherein V8 proteinase digestion of the enzyme produces at least one fragment having a sequence selected from the group consisting of ENYPLD (Seq. ID. No. 2), EKFLKGNIOD (Seq. ID. No. 3), EVIDGANVH (Seq. ID. No. 4), EANGDDF (Seq. ID. No. 5), EQVITON (Seq. ID. No. 6), EAGDGXD (Seq. ID. No. 7), EAMNNPFD (Seq. ID. No. 8), and KOLGND (Seq. ID. No. 9).

* * * * *